US012622877B2

(12) United States Patent
Guo et al.

(10) Patent No.: US 12,622,877 B2
(45) Date of Patent: May 12, 2026

(54) NANOCOMPOSITE AND PREPARATION METHOD AND USE THEREOF

(71) Applicant: Qilu University of Technology (Shandong Academy of Sciences), Jinan (CN)

(72) Inventors: Yingshu Guo, Jinan (CN); Wenxin Li, Jinan (CN)

(73) Assignee: Qilu University of Technology (Shandong Academy of Sciences), Jinan (CN)

( * ) Notice: Subject to any disclaimer, the term of this patent is extended or adjusted under 35 U.S.C. 154(b) by 542 days.

(21) Appl. No.: 18/251,185

(22) PCT Filed: Nov. 25, 2022

(86) PCT No.: PCT/CN2022/134412
§ 371 (c)(1),
(2) Date: Apr. 28, 2023

(87) PCT Pub. No.: WO2024/087292
PCT Pub. Date: May 2, 2024

(65) Prior Publication Data
US 2024/0342103 A1      Oct. 17, 2024

(30) Foreign Application Priority Data

Oct. 26, 2022    (CN) .......................... 202211315441.1

(51) Int. Cl.
*A61K 9/50*        (2006.01)
*A61P 35/00*       (2006.01)
(52) U.S. Cl.
CPC ............ *A61K 9/5068* (2013.01); *A61P 35/00* (2018.01)

(58) Field of Classification Search
None
See application file for complete search history.

(56) References Cited

FOREIGN PATENT DOCUMENTS

| CN | 107837404 A | * | 3/2018 | ............. A61K 51/04 |
| CN | 107890566 A | * | 4/2018 | ......... A61K 41/0057 |
| WO | WO-2020223454 A1 | * | 11/2020 | ........... C12Q 1/6883 |

* cited by examiner

*Primary Examiner* — Christopher M Babic
(74) *Attorney, Agent, or Firm* — Knobbe, Martens, Olson & Bear LLP

(57)        ABSTRACT

The present disclosure provides a nanocomposite and a preparation method and use thereof. In the present disclosure, the nanocomposite is wrapped with Prussian blue nanoparticles (PB) using a platelet membrane (PM) as a shell; and a surface of the PM is modified with an aptamer of cancer cells and horseradish peroxidase (HRP). An ability of platelets (PLTs) to specifically target cancer cells and inflammatory sites can effectively enhance the accumulation of nanoparticles at tumor sites, and help PB better achieve a desirable photothermal therapy (PTT) under near-infrared light irradiation. In addition, hydrogen peroxide is highly expressed in the tumor microenvironment; the HRP modified on a surface of the nanocomposite can decompose the hydrogen peroxide to generate oxygen bubbles, which drive active transport of the nanocomposite, thereby enhancing the accumulation in cancer cells. Modification with the aptamer of cancer cells on a platelet membrane surface enhances cancer cell targeting.

20 Claims, 11 Drawing Sheets
Specification includes a Sequence Listing.

PB/PM           PM           PB

SEQUENCE LISTING

```
Sequence total quantity: 1
SEQ ID NO: 1          moltype = DNA  length = 26
FEATURE               Location/Qualifiers
source                1..26
                      mol_type = other DNA
                      organism = synthetic construct
SEQUENCE: 1
ggtggtggtg gttgtggtgg tggtgg                                    26
```

NANOCOMPOSITE AND PREPARATION METHOD AND USE THEREOF

CROSS REFERENCE TO RELATED APPLICATION

The present application is a U.S. National Phase application of PCT International Application Number PCT/CN2022/134412, filed on Nov. 25, 2022, which claims priority to the Chinese Patent Application No. 202211315441.1, filed with the China National Intellectual Property Administration (CNIPA) on Oct. 26, 2022, and entitled "NANOCOMPOSITE AND PREPARATION METHOD AND USE THEREOF", which is incorporated herein by reference in its entirety.

REFERENCE TO SEQUENCE LISTING

A computer readable XML file entitled "BGI021_001APC", that was created on Apr. 24, 2023, with a file size of about 2,013 bytes, contains the sequence listing for this application, has been filed with this application, and is hereby incorporated by reference in its entirety.

TECHNICAL FIELD

The present disclosure belongs to the technical field of biomedicine, and in particular relates to a nanocomposite and a preparation method and use thereof.

BACKGROUND

Cancer medically refers to malignant tumors originating from epithelial tissue, and is the most common type of malignant tumors. Cancer is still a big problem in medicine until now. Although scientists continue to explore and make great achievements in this field, there are still many unknown problems to be solved. The ideal outcome of an effective anticancer therapy should include the elimination of primary tumors and the sustained suppression of development of metastatic tumors. Currently, the commonly used treatment methods include surgery, chemotherapy, phototherapy, and immunotherapy.

However, the tumor microenvironment is characterized by dense extracellular matrix, elevated interstitial fluid pressure, hypoxia, and avascular zones. This specificity limits the delivery of nanomaterials to tumor cells, leading to extravasation of nanomaterials back into the bloodstream. Due to the particularity of the above-mentioned tumor sites, exploratory studies have determined that monotherapy is difficult to achieve a desirable tumor elimination effect, let alone inhibit primary tumor metastasis. Therefore, in order to improve the therapeutic efficacy against tumor cells, multimodal synergistic therapy is urgently needed.

SUMMARY

A purpose of the present disclosure is to study a nanocomposite and a preparation method and use thereof. In the present disclosure, the accumulation of Prussian blue nanocomposites in tumor sites can be effectively enhanced and a targeting effect on tumor cells can be enhanced.

The present disclosure provides a nanocomposite, where the nanocomposite material is composed of prussian blue nanoparticles wrapped by platelet membrane, and a surface of the platelet membrane is modified with an aptamer of cancer cells and horseradish peroxidase.

Preferably, the cancer cells include breast cancer cells.

Preferably, an aptamer of the breast cancer cells includes an AS1411 aptamer.

The present disclosure further provides a preparation method of the nanocomposite, including the following steps:

1) mixing the platelet membrane and the Prussian blue nanoparticles to obtain PB/PM nanoparticles;

2) attaching the PB/PM nanoparticles to a well plate with a layer of polylysine at a bottom, and adding the horseradish peroxidase to the well plate; subjecting the horseradish peroxidase and the PB/PM nanoparticles to dehydration condensation; and separating a product after the dehydration condensation from the well plate to obtain PB/PM/HRP;

3) mixing the PB/PM/HRP and the aptamer of cancer cells to obtain the nanocomposite.

Preferably, the platelet membrane is prepared from platelets; 80 µL to 120 µL of the platelet membrane is prepared from per $1*10^6$ of the platelets; the Prussian blue nanoparticles are dissolved in a phosphate-buffered saline (PBS), with a concentration of 0.5 mg/mL to 0.6 mg/mL; and the platelet membrane and the Prussian blue nanoparticles have a volume ratio of (1.2-1.5):1.

Preferably, the aptamer of cancer cells is a carboxyl-modified aptamer of cancer cells.

Preferably, the PB/PM/HRP and the aptamer of cancer cells have a mass ratio of (65-70):1.

Preferably, the horseradish peroxidase is labeled with biotin; and the PB/PM nanoparticles and the biotin-labeled horseradish peroxidase have a mass ratio of (55-60):1.

The present disclosure further provides use of the nanocomposite or a nanocomposite prepared by the preparation method in preparation of an antitumor drug.

The present disclosure provides a nanocomposite, where the nanocomposite uses platelet membrane (PM) as a shell to wrap Prussian blue nanoparticles (PB); and a surface of the platelet membrane is modified with an aptamer of cancer cells and horseradish peroxidase (HRP). In the present disclosure, PB that has a desirable light-to-heat conversion efficiency and PM that protects the nanomaterial from immune clearance are combined. An ability of platelets (PLTs) to specifically target cancer cells and inflammatory sites can effectively enhance the accumulation of nanoparticles at tumor sites, and achieve a desirable photothermal therapy (PTT) under near-infrared light irradiation. In addition, hydrogen peroxide is highly expressed in the tumor microenvironment; the HRP modified on a surface of the nanocomposite can decompose the hydrogen peroxide to generate oxygen bubbles; the oxygen bubbles drive active transport of the nanocomposite, and the HRP can act as a chemical driver, thereby enhancing the accumulation in cancer cells. Modification of the platelet membrane surface with a cancer cell aptamer enhanced the targeting of the nanocomposite to cancer cells.

BRIEF DESCRIPTION OF THE DRAWINGS

To describe the embodiments of the present disclosure or the technical solutions in the related art more clearly, the accompanying drawings required in the embodiments are briefly introduced below. Obviously, the accompanying drawings described below are only some embodiments of the present disclosure. A person of ordinary skill in the art may further obtain other accompanying drawings based on these accompanying drawings without creative labor.

FIG. 4A is the particle size distribution of PB, and FIG. 4B is the particle size distribution of PB/PM;

DETAILED DESCRIPTION OF THE EMBODIMENTS

Figure 1:
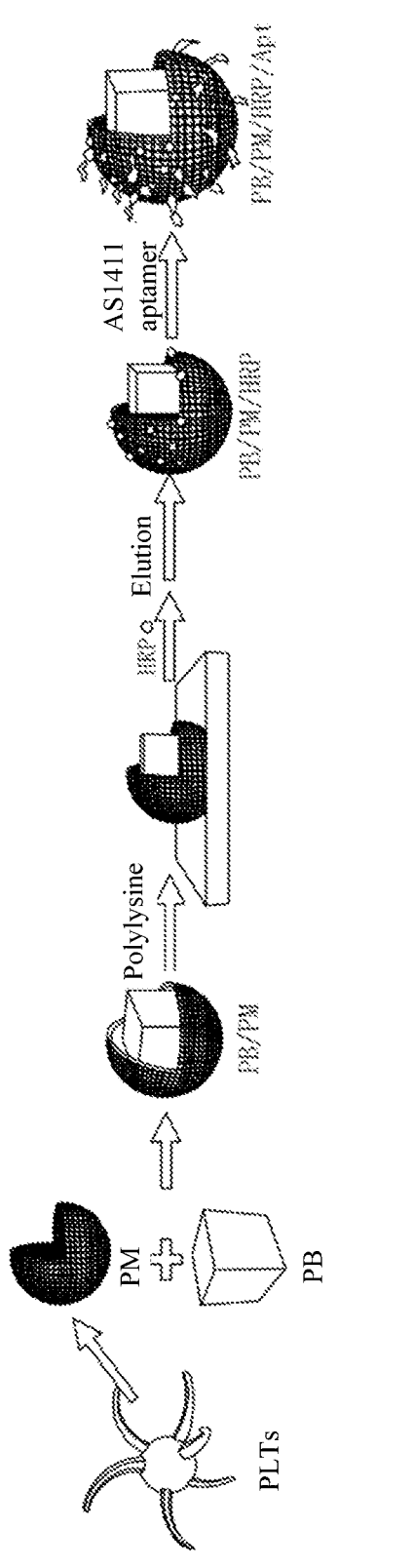
FIG. 1 shows a schematic diagram of the synthesis of PB/PM/HRP/Apt.

The present disclosure provides a nanocomposite, where the nanocomposite material is composed of prussian blue nanoparticles wrapped by platelet membrane, and a surface of the platelet membrane is modified with an aptamer of cancer cells and horseradish peroxidase.

In the present disclosure, the nanocomposite has a core-shell structure.

In the present disclosure, the platelet membrane is prepared from platelets; 80 μL to 120 μL of the platelet membrane is prepared from per $1*10^6$ of the platelets, more preferably 100 μL of the platelet membrane is prepared from per $1*10^6$ of the platelets; there is no special limitation on a method for preparing the platelet membranes from platelets, and conventional methods in the art can be used; in a specific example, the platelet membrane is preferably prepared by repeated freezing and thawing. The platelet membrane has inherent tumor homing performance, can specifically target tumor sites, and effectively enhances the accumulation of nanoparticles in tumor sites.

In the present disclosure, the Prussian blue nanoparticles have an encapsulation amount of preferably 0.5 mg/mL to 0.6 mg/mL. As a photothermal agent, the Prussian blue nanoparticles can convert light energy into heat energy to kill tumor cells under external light sources such as near-infrared. Therefore, the nanocomposite achieves a desirable photothermal performance under the irradiation of near-infrared light.

In the present disclosure, the cancer cells preferably include breast cancer cells; an aptamer of the breast cancer cells includes preferably an AS1411 aptamer; and the AS1411 aptamer has a nucleotide sequence shown in SEQ ID NO: 1, specifically: 5'-COOH-GGTGGTGGTGG-TTGTGGTGGTGGTGG-3'. The aptamer of cancer cells enhances cancer cell targeting of the nanocomposite.

In the present disclosure, hydrogen peroxide is highly expressed in the tumor microenvironment; the HRP modified on a surface of the nanocomposite can decompose the hydrogen peroxide to generate oxygen bubbles; the oxygen bubbles drive active transport of the nanocomposite, and the HRP can act as a chemical driver, thereby enhancing the accumulation of nanocomposite in cancer cells.

In the present disclosure, the nanocomposite is prepared by wrapping Prussian blue nanoparticles with the platelet membrane. Since the platelet membrane has intrinsic tumor-homing properties and can specifically target tumor sites, the membrane-encapsulated nanocomplexes are homologous. According to the inherent tumor-homing ability and excellent biocompatibility of platelets, the homologous nanocomposite has desirable stability, targeting, intelligence, and high bioavailability. By functionalizing the surface of PB with desirable photothermal performance, PM with cancer cell targeting and immune escape ability is coated, and a surface of the PM is modified with an aptamer of 4T1 cells and HRP. PB/PM/HRP/Apt can more easily evade immune clearance and target tumor tissue, and this specific targeting method can significantly enhance the accumulation of PB/PM/HRP/Apt in tumor sites, providing a new idea for the development of various nanocarriers in the field of biomedicine.

The present disclosure further provides a preparation method of the nanocomposite, including the following steps:

1) mixing the platelet membrane and the Prussian blue nanoparticles to obtain PB/PM nanoparticles;

2) attaching the PB/PM nanoparticles to a well plate with a layer of polylysine at a bottom, and adding the horseradish peroxidase to the well plate; subjecting the horseradish peroxidase and the PB/PM nanoparticles to dehydration condensation; and separating a product after the dehydration condensation from the well plate to obtain PB/PM/HRP;

3) mixing the PB/PM/HRP and the aptamer of cancer cells to obtain the nanocomposite.

In the present disclosure, the platelet membrane and the Prussian blue nanoparticles are mixed to obtain PB/PM nanoparticles.

In the present disclosure, the Prussian blue nanoparticles are dissolved in a PBS; the platelet membrane and the Prussian blue nanoparticles have a volume ratio of preferably (1.2-1.5):1; and the Prussian blue nanoparticles have a concentration of preferably 0.5 mg/mL to 0.6 mg/mL.

In the present disclosure, there is no special limitation on a source of the Prussian blue nanoparticles, which may be prepared by conventional methods in the art or obtained from commercially available sources.

In the present disclosure, the PB/PM nanoparticles are attached to a well plate with a layer of polylysine at a bottom, and the horseradish peroxidase is added to the well plate; the horseradish peroxidase and the PB/PM nanoparticles are subjected to dehydration condensation; and a product after the dehydration condensation is separated from the well plate to obtain PB/PM/HRP.

In the present disclosure, the horseradish peroxidase is labeled with biotin; and the PB/PM nanoparticles and the biotin-labeled horseradish peroxidase have a mass ratio of (55-60):1.

In the present disclosure, the PB/PM/HRP and the aptamer of cancer cells are mixed to obtain the nanocomposite.

In the present disclosure, the aptamer of cancer cells is preferably a carboxyl-modified aptamer. Under the action of an activator, amino groups on the platelet membrane are subjected to dehydration condensation with the aptamer of cancer cells modified with carboxyl groups, such that the surface of the platelet membrane is modified with the aptamer of cancer cells.

In the present disclosure, the carboxyl groups are modified on the aptamer targeting cancer cells, and the horseradish peroxidase has its own carboxyl groups. Therefore, the amino groups on the platelet membrane can be subjected to dehydration condensation with the carboxyl groups of horseradish peroxidase and the carboxyl groups modified on the aptamer of cancer cells, such that the surface of the platelet membrane is modified with the horseradish peroxidase and the adapter of cancer cells.

In the present disclosure, the activator is preferably N-(3-dimethylaminopropyl)-N'-ethyl carbodiimide hydrochloride (EDC) and N-hydroxysuccinimide (NHS).

In the present disclosure, the PB/PM/HRP and the aptamer of cancer cells have a mass ratio of (65-70):1.

The present disclosure further provides use of the nanocomposite or a nanocomposite prepared by the preparation method in preparation of an antitumor drug.

In order to further illustrate the present disclosure, the nanocomposite and the preparation method and the use thereof provided in the present disclosure are described in detail below with reference to examples, but the examples should not be interpreted as a limitation to the protection scope of the present disclosure.

Example 1

1. Materials and Reagents

Polyvinylpyrrolidone (PVP) was purchased from Shanghai YuanYe Bio-Technology Co., Ltd. K3[Fe(CN)$_6$] was purchased from Shanghai Macklin Biochemical Co., Ltd. EDC and NHS were purchased from Shanghai Aladdin Biochemical Technology Co., Ltd. FITC-labeled streptavidin and HRP-labeled biotin were purchased from Sangon Biotech (Shanghai) Co., Ltd. The AS1411 aptamer (5'-COOH-GGTGGTGGTGGTTGTGGTGGTGGTGG-3', SEQ ID NO: 1) was purchased from Sangon Biotech (Shanghai) Co., Ltd. Hoechst 33342 was provided by Beijing Solarbio Technology Co., Ltd. Calcein AM/PI cell viability and cytotoxicity detection kit was purchased from Shanghai Beyotime Biotech Co., Ltd. Cell proliferation/toxicity detection kit (CCK-8) was purchased from Dojindo Molecular Technologies (Shanghai) Co., Ltd. A 300-mesh copper mesh was purchased from ProSciTech. All other reagents were of analytical grade and used directly without further purification. All water used in experiment was sterilized ultrapure water. All glassware was washed with fresh aqua regia (HCl/HNO$_3$=3:1, v/v) before use.

2. Instruments

Products were characterized by a transmission electron microscope (TEM) (JEM-2100, JEOL). Fluorescence was measured using an F-4600 spectrofluorometer (Hitachi). An average particle size and a Zeta potential were measured by dynamic light scattering (DLS), and confocal fluorescence imaging study was conducted using a confocal laser scanning microscopy (CLSM) (Nikon C2 plus) with an objective lens (×20).

3. Synthesis of PB

PVP (3 g) was placed in a 100 mL round bottom flask at room temperature and dissolved in deionized water under magnetic stirring. HCl (0.8 mL, 0.1 M) and K3[Fe(CN)$_6$] (264 mg) were added to an obtained solution with continuous stirring. The round bottom flask was transferred to a constant-temperature oil bath for treating at 80° C. for 20 h with stirring. The obtained PB was isolated and purified by centrifugation with absolute ethanol and deionized water. The PB was dispersed in 10 mL of deionized water for future use.

4. Acquisition of PM

Platelets were isolated from whole blood by gradient centrifugation. Briefly, 10 mL of whole blood was centrifuged at 200 g for 10 min. A supernatant was separated as platelet-rich plasma (PRP). PRP was centrifuged at 1,800 g for 20 min, a pellet was washed with PBS and centrifuged repeatedly, and then platelets were obtained. The platelets were frozen at 80° C. and thawed at room temperature. The above freeze-thaw process was repeated three times. The platelet membrane was obtained by centrifugation at 8,000 rpm for 10 min, washed with PBS containing a protease inhibitor, and sonicated with a sonicator for 5 min.

5. Synthesis of PB/PM Nanoparticles

A certain amount of PM was mixed with PB, and a resulting mixture was sonicated for 35 min to obtain PB/PM. In order to maintain the activity of membrane proteins, ice was added during the sonication. The freshly prepared PB/PM was placed in a 1×PBS buffer overnight at 4° C. The PB/PM was centrifuged at 8,000 rpm for 6 min in a centrifuge tube, and a liquid was sucked out, and a precipitate was dissolved in the PBS solution. The above operation was repeated three times to remove excess cell membranes to obtain purified PB/PM.

6. Synthesis of PB/PM/HRP/Apt

PB/PM/HRP/Apt was fabricated on a commercial polylysine (PLL)-modified 12-well plate. To complete the surface modification, PB/PM was attached to the PLL surface by centrifugation at 900 rpm for 3 min. After incubation for 1 h at room temperature, a supernatant was removed and the plate was washed three times with PBS to remove all unattached PB/PM. Centrifugation allowed the PB/PM fraction to soak into the PLL layer at the bottom of the 12-well plate, while subsequent incubation enhanced the electrostatic attachment between the positively-charged PLL surface and the negatively-charged platelet membrane. This process partially blocked the platelet membrane and allowed subsequent immobilization of horseradish catalase. 10 µL of EDC with a concentration of 0.5 mM and 10 µL of an NHS solution with a concentration of 0.5 mM were separately added to the reaction system as activators and incubated for 30 min. After incubation with HRP-labeled biotin and FITC-labeled streptavidin sequentially for 30 min at room temperature, a supernatant was removed, and the PLL was washed three times with PBS to remove all unattached reagents. A product was detached from the PLL surface by gentle repeated pipetting followed by two PBS washes to obtain fluorophore FITC-modified PB/PM/HRP. The AS1411 aptamer was introduced to obtain the nanocomposite PB/PM/HRP/Apt.

7. Cell Cultivation

All 4T1 cells involved in the experiment were cultured in an incubator with a constant temperature at 37° C. and a humidity of 95% and a CO2 concentration of 5%. The cell medium was DMEM containing 10% fetal bovine serum and 1% double antibody (penicillin-streptomycin).

8. Photothermal Efficiency Test of the Material

The photothermal efficiency test was conducted by irradiating PB and PB/PM/HRP/Apt material with a same concentration by an 808 nm laser at a power of 2 W cm$^{-2}$ for 10 min. Images at different time points were collected using an infrared thermal imager, and a temperature change curve at different time periods was obtained by a data processing system.

9. CCK-8 Analysis

Cytotoxicity of the nanocomposite to cells was assessed by CCK-8 assay. 4T1 cells were inoculated in a 96-well plate with a cell density of 10,000 cells per well. 10 µL of nanocomplexes with different concentrations were added to the 96-well plate, and the 96-well plate was incubated at 37° C. for 4 h. A supernatant was carefully removed, 100 µL of a fresh medium (containing 10% CCK-8 solution) was added, and incubation was continued for 35 min. An absorbance at 450 nm was measured with a microplate reader.

10. Cell Internalization Test

In order to study the uptake of nanocomposite in cells, after culturing 4T1 cells in a confocal dish for about 12 h, PB/PM/HRP/Apt was added to the cells and incubated for 30 min, 2 h, and 4 h separately. After staining with Hoechst 33342 for about 10 min, the cells were thoroughly washed with PBS, and the internalization of nanocomposite in cells was detected by CLSM.

Results and Discussion:

1. Characterization of PB/PM/HRP/Apt

Figure 2:
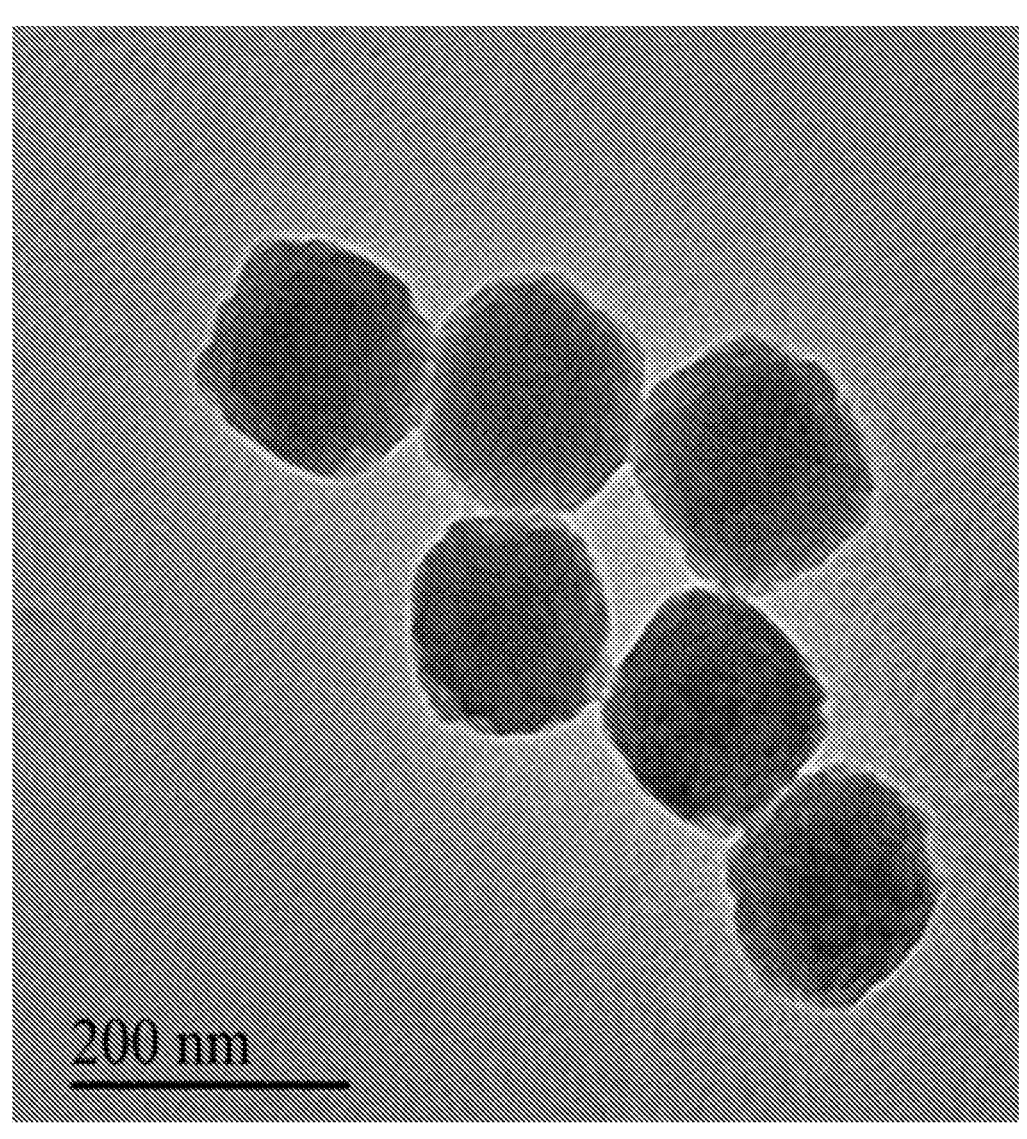
FIG. 2 shows a transmission electron microscopy (TEM) image of PB.
Figure 3:
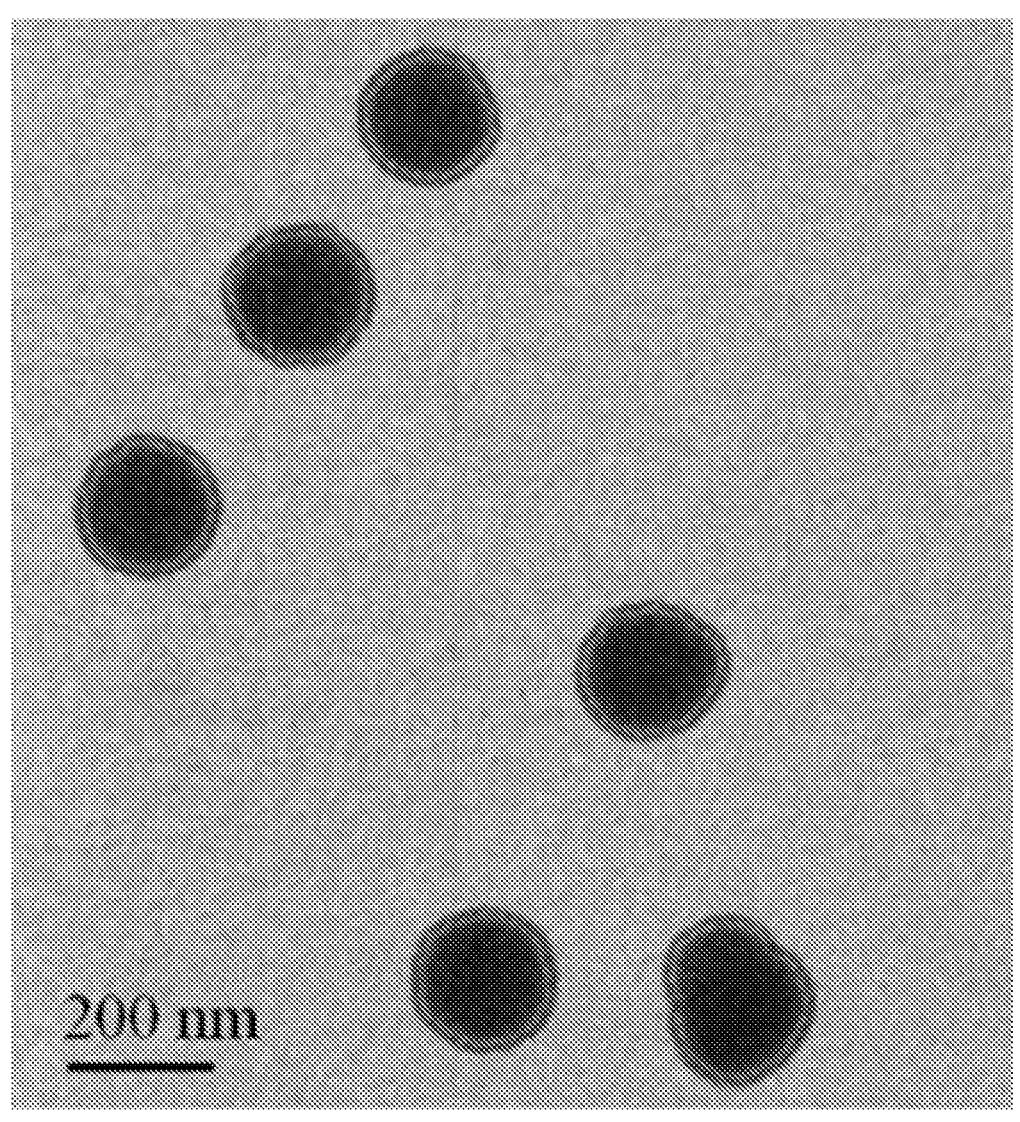
FIG. 3 shows a TEM image of PB/PM.
Figure 4A:
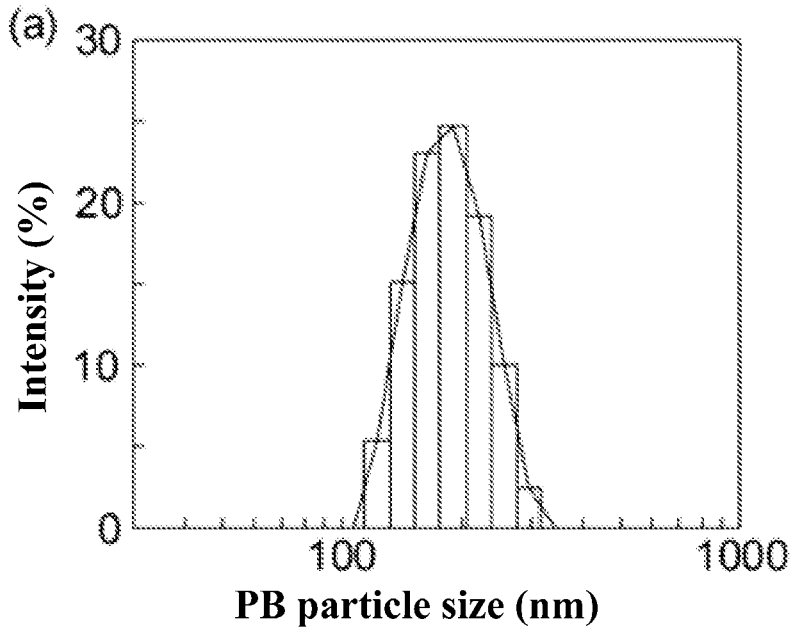
FIG. 4A-B show particle size distribution of different particles, where
Figure 4B:
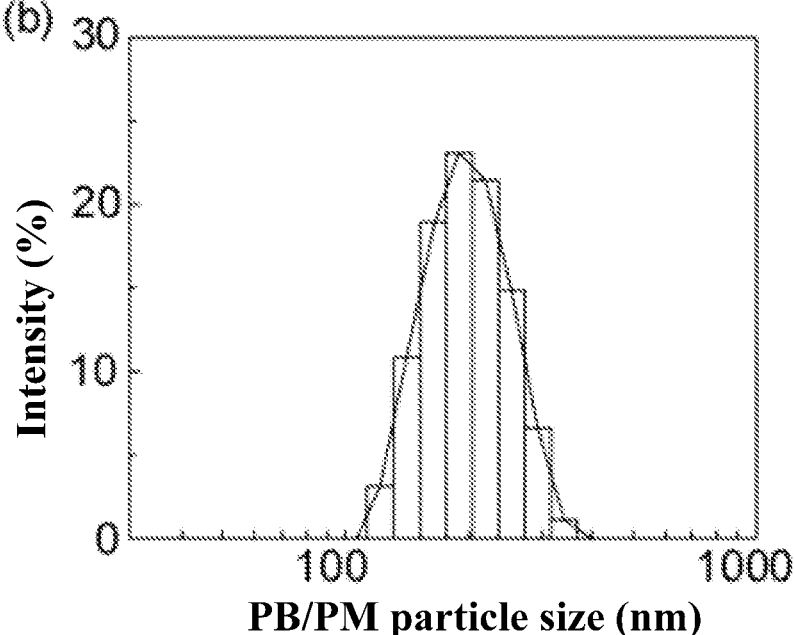
Figure 5:
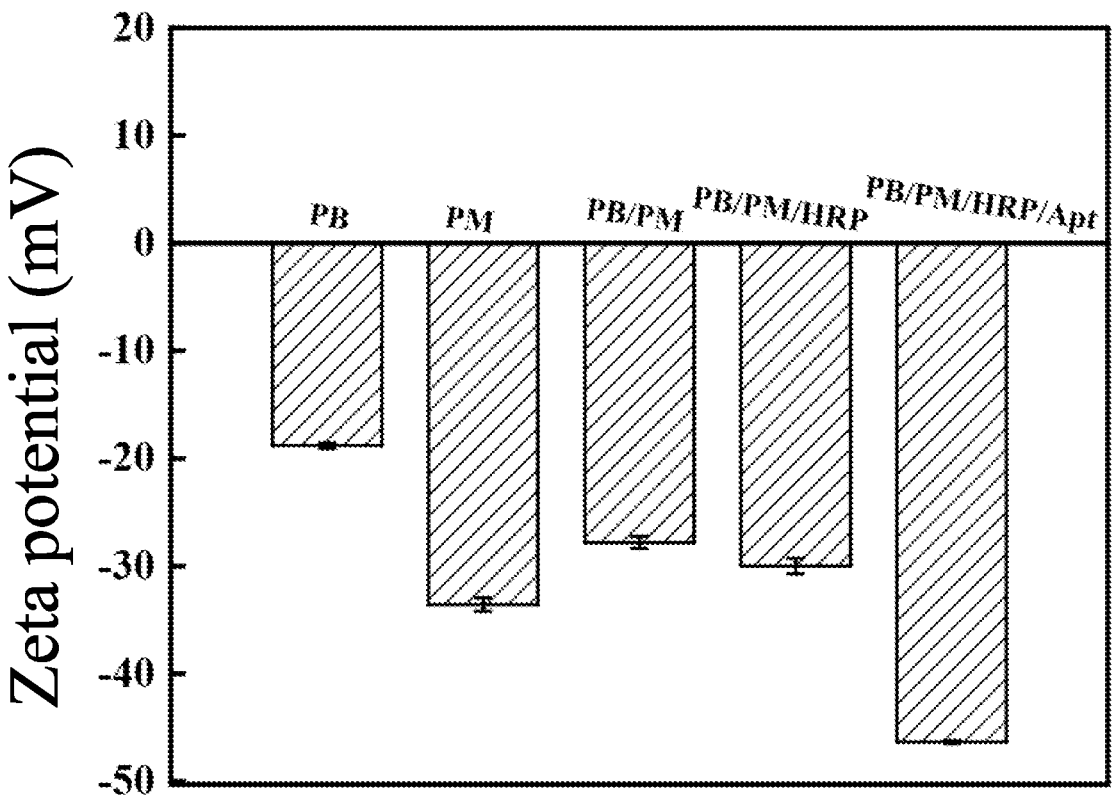
FIG. 5 shows potential changes of PB, PM, PB/PM, PB/PM/HRP, and PB/PM/HRP/Apt.

In an acidic environment, with $[Fe(CN)_6]^{3-}$ as a precursor and polyvinylpyrrolidone (PVP) as a protective agent, ferrous ions were slowly released and oxidized into ferric ions. The formed iron ions could react with undecomposed ions to form PB. Due to a slow reaction process and the high monodispersity of the formed PB, this method was considered to be the best method for preparing PB. Based on the synthesis of PB, PB/PM was obtained by ultrasonic method. Primary amines of cell membrane proteins provided stable anchors for cell surface engineering. With EDC and NHS as activators, the fluorescein isothiocyanate (FITC)-modified HRP was immobilized on the surface of PB/PM. The carboxyl-modified AS1411 aptamer was introduced to obtain PB/PM/HRP/Apt (FIG. 1). Through TEM images, it was found that PB had a uniform distribution and a uniform size, with an average size of about 182 nm (FIG. 2). A clear core-shell structure was seen in the TEM images of PB/PM, with an average size of about 193 nm, and PM had a thickness of about 9 nm (FIG. 3). To further verify the successful coating of PB/PM/HRP/Apt, the particle size and Zeta potential were analyzed by dynamic light scattering (DLS). The PB/PM/HRP/Apt had a hydrodynamic diameter increased to around 230 nm (Table 1 and FIGS. 4A-B), and the Zeta potential decreased from −18.8 mV of PB to around −46.3 mV (Table 2 and FIG. 5).

TABLE 1

Particle size distribution of PB, PM,
PB/PM, PB/PM/HRP, and PB/PM/HRP/Apt

| Type | PB | PB/PM | PB/PM/HRP | PB/PM/HRP/Apt |
|---|---|---|---|---|
| Particle size (nm) | 181.4 | 193.6 | 203.4 | 230.0 |

TABLE 2

Potential changes of PB, PM, PB/PM,
PB/PM/HRP, and PB/PM/HRP/Apt

| Type | PB | PM | PB/PM | PB/PM/HRP | PB/PM/HRP/Apt |
|---|---|---|---|---|---|
| Zeta potential (mV) | −18.8 | −33.6 | −27.8 | −30.0 | −46.3 |

Figure 6:
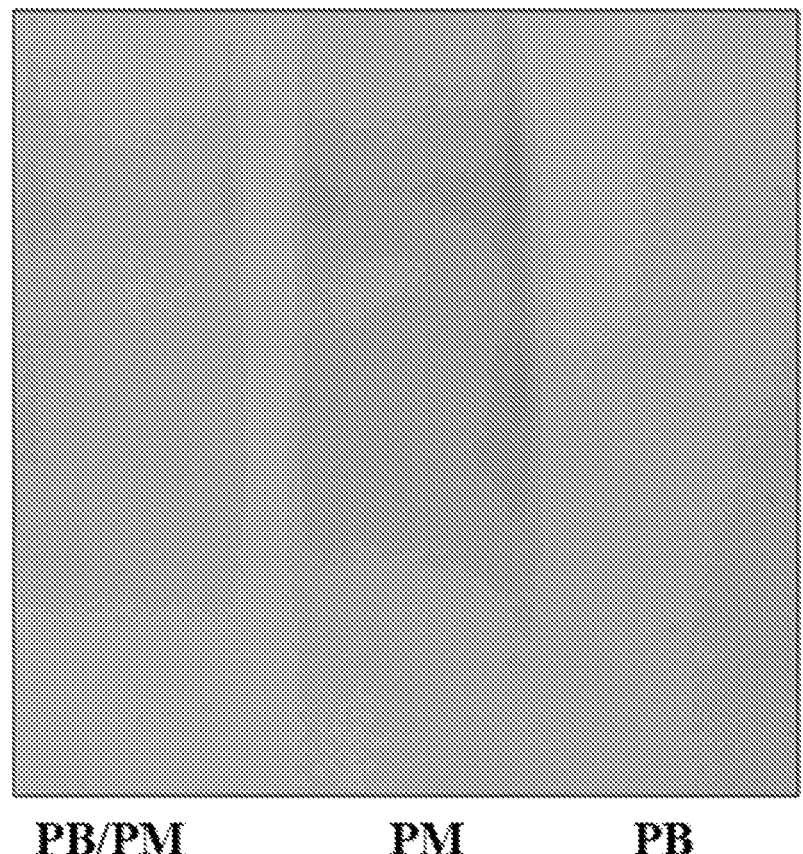
FIG. 6 shows sodium dodecyl sulfate polyacrylamide gel electrophoresis (SDS-PAGE) images of PB, PM, PB/PM.
Figure 7:
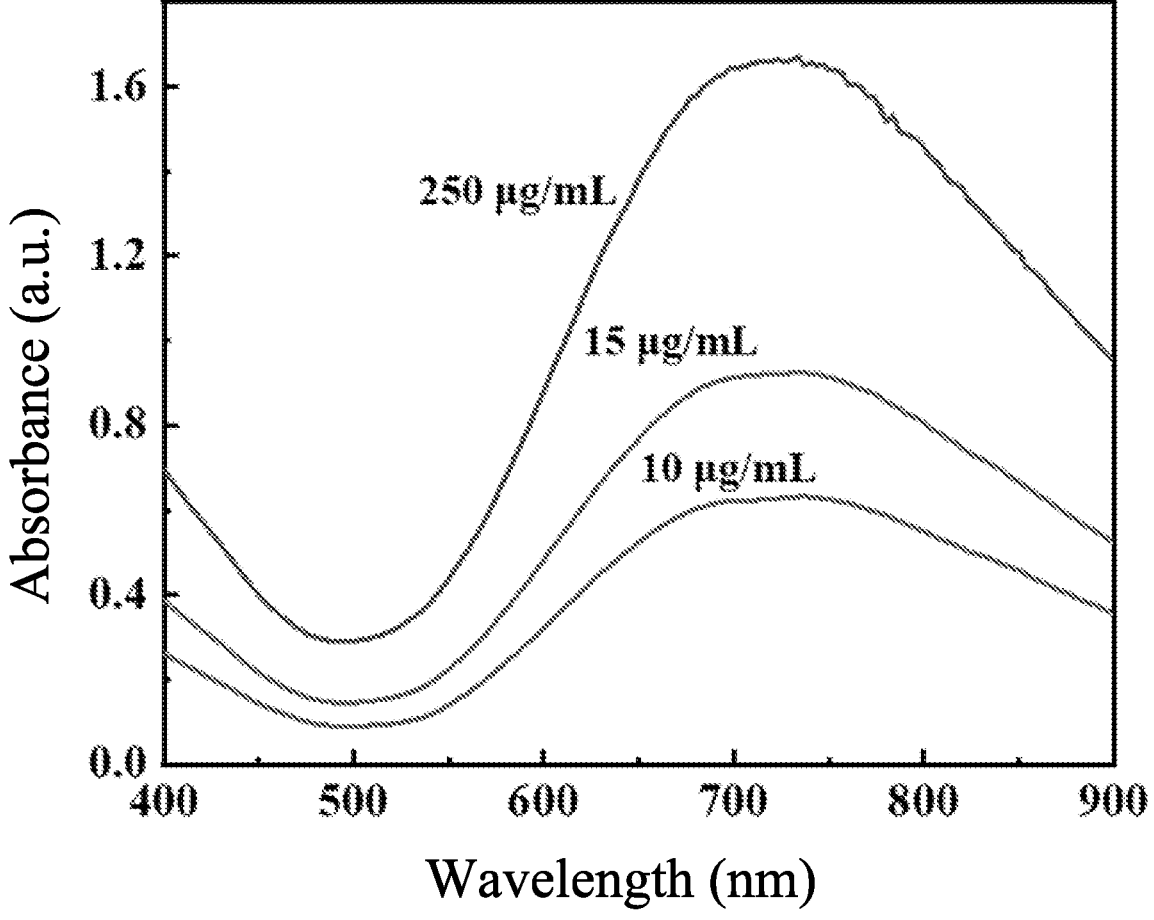
FIG. 7 shows ultraviolet-visible absorption spectra of PB with different concentrations.
Figure 8:
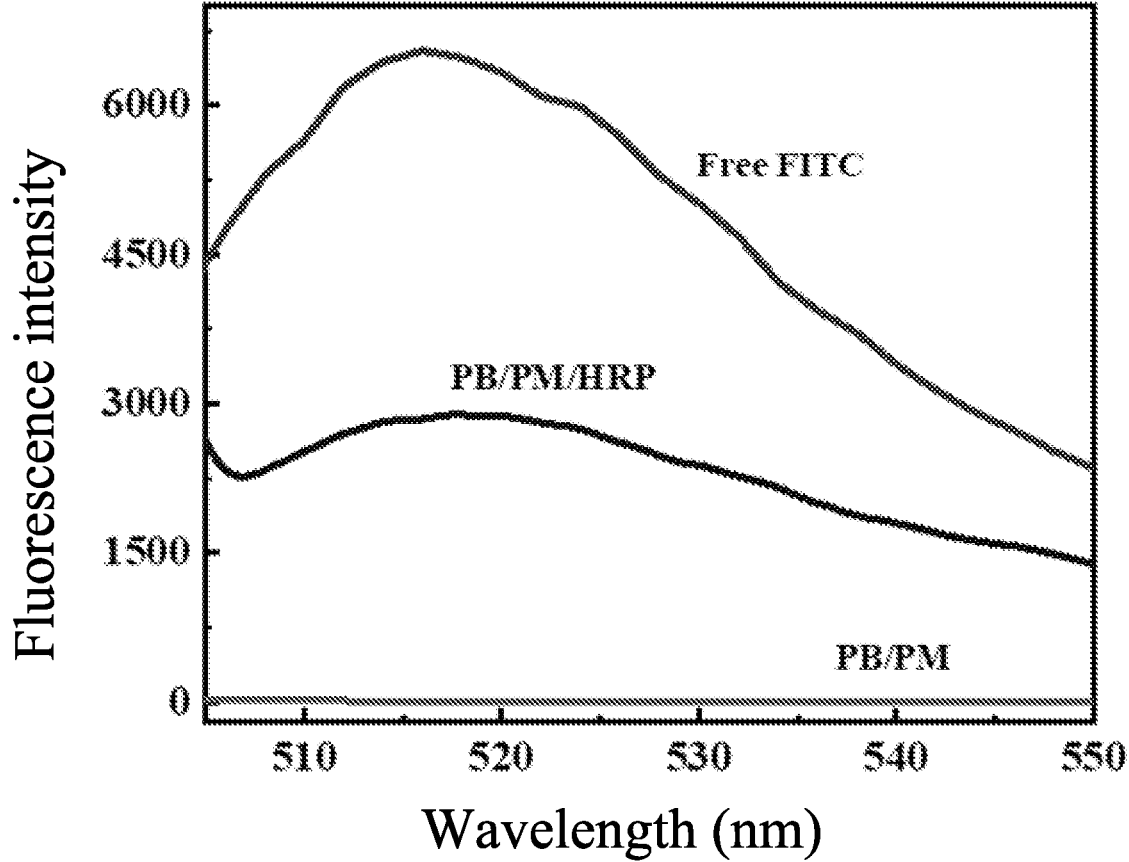
FIG. 8 shows fluorescence spectra of free FITC, PB/PM/HRP, and PB/PM.

SDS-PAGE was conducted to determine whether the surface proteins of the cell membrane could be maintained on PB/PM. As shown in FIG. 6, PB/PM and PM showed similar protein profiles, indicating that the protein was fully retained in PB/PM. However, bands for the HRP fraction could not be found in the gel electrophoresis analysis because their content was much lower than that of the protein present on the platelet surface. These results indicated that HRP could be used to modify the surface of nanomaterial without changing their protein profiles, which was a prerequisite for the subsequent biomedical application of PB/PM/HRP/Apt. Meanwhile, ultraviolet-visible spectrophotometry (UV-Vis) analysis demonstrated the successful preparation of PB and PB/PM/HRP/Apt. In UV-Vis analysis, PB had a strong absorbance in the range of 650 nm to 800 nm, which was the characteristic peak of PB, proving that the synthesis of PB was successful. Moreover, the absorption peak at 650 nm to 800 nm also showed that the PB could convert light energy into thermal energy under the 808-nm laser irradiation, so as to be used in subsequent photothermal therapy (FIG. 7). In addition, since the surface of HRP was modified by the fluorophore FITC, the synthesized PB/PM/HRP was fluorescent. In the fluorescence spectrum, the fluorescence signal of FITC was detected in PB/PM/HRP, but no fluorescence signal of FITC was detected in unmodified PB, indicating that the nanomaterial was successfully loaded with HRP (FIG. 8). The above series of results indicated that PB/PM/HRP/Apt was successfully prepared.

2. Photothermal Performance Evaluation of PB/PM/HRP/Apt

To characterize the photothermal performance, the photothermal conversion effect of PB/PM/HRP/Apt was verified in vitro. PB/PM/HRP/Apt was irradiated with near-infrared laser at 808 nm for 10 min at a power density of 2 W cm-2, and the temperature of a PB/PM/HRP/Apt dispersion during laser irradiation was also monitored in real time by an infrared thermal imager. It was concluded that the temperature curve showed a concentration-dependent increase when the concentration of PB/PM/HRP/Apt increased, indicating that the temperature increase was positively correlated with the concentration of PB/PM/HRP/Apt; and the PB/PM/HRP/Apt with a concentration of 0.6 mg/mL could reach an optimal temperature for tumor treatment after 5 min.

Figure 9:
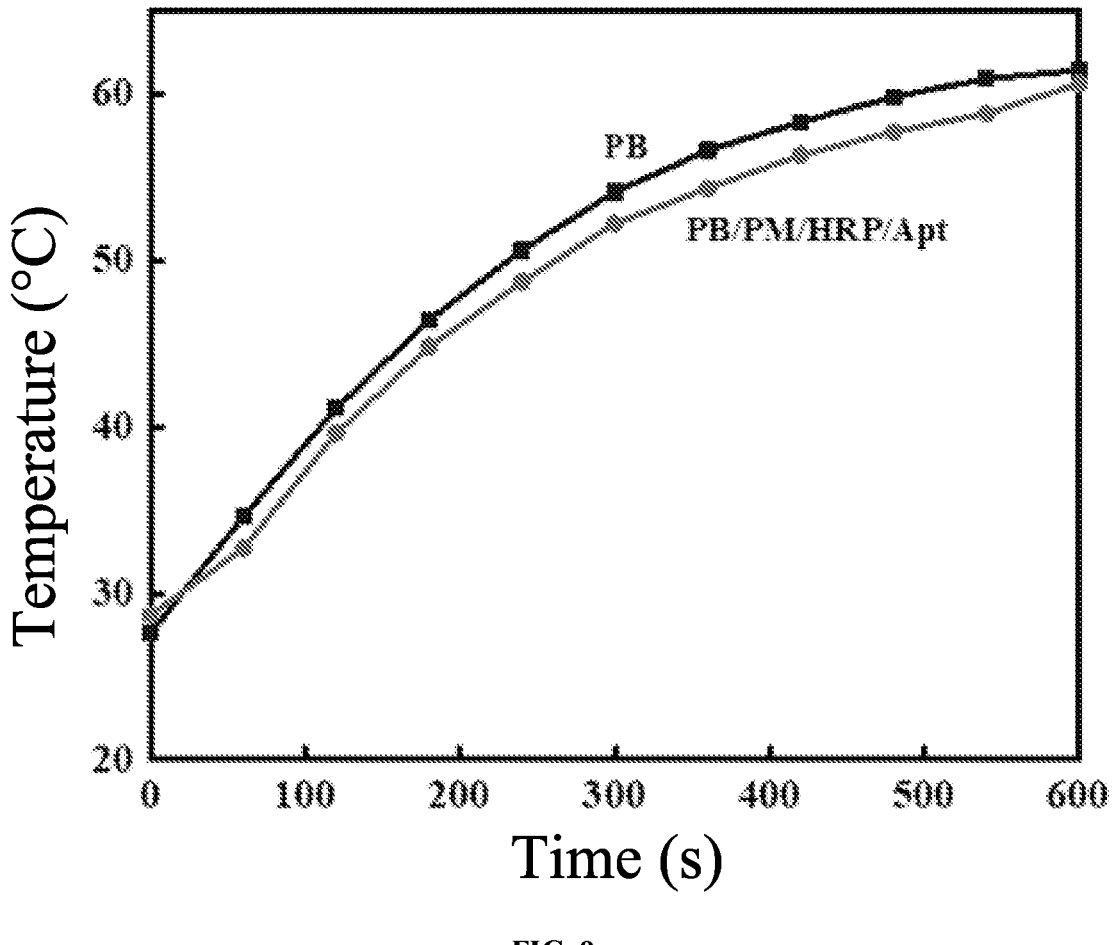
FIG. 9 shows temperature rise curves of PB and PB/PM/HRP/Apt under laser irradiation at 808 nm for 10 min.

Meanwhile, after irradiating PB and PB/PM/HRP/Apt at a concentration of 0.6 mg/mL with a same power density for 10 min, temperatures of the two increased rapidly; after 10 min, the temperature of PB increased to about 61° C., and that of PB/PM/HRP/Apt increased to 60° C. A temperature difference between the two was not obvious and tended to be stable gradually (FIG. 9). The above results showed that the nanocomposite coated with other substances still had high photothermal conversion performance, and the coating of cell membrane, HRP and aptamer had little effect on the photothermal effect of PB. In conclusion, PB/PM/HRP/Apt had obvious photothermal conversion efficiency and could be used as a photothermal agent to kill cancer cells by thermal ablation.

3. In Vitro Anti-Tumor Cell Efficacy

Figure 10:
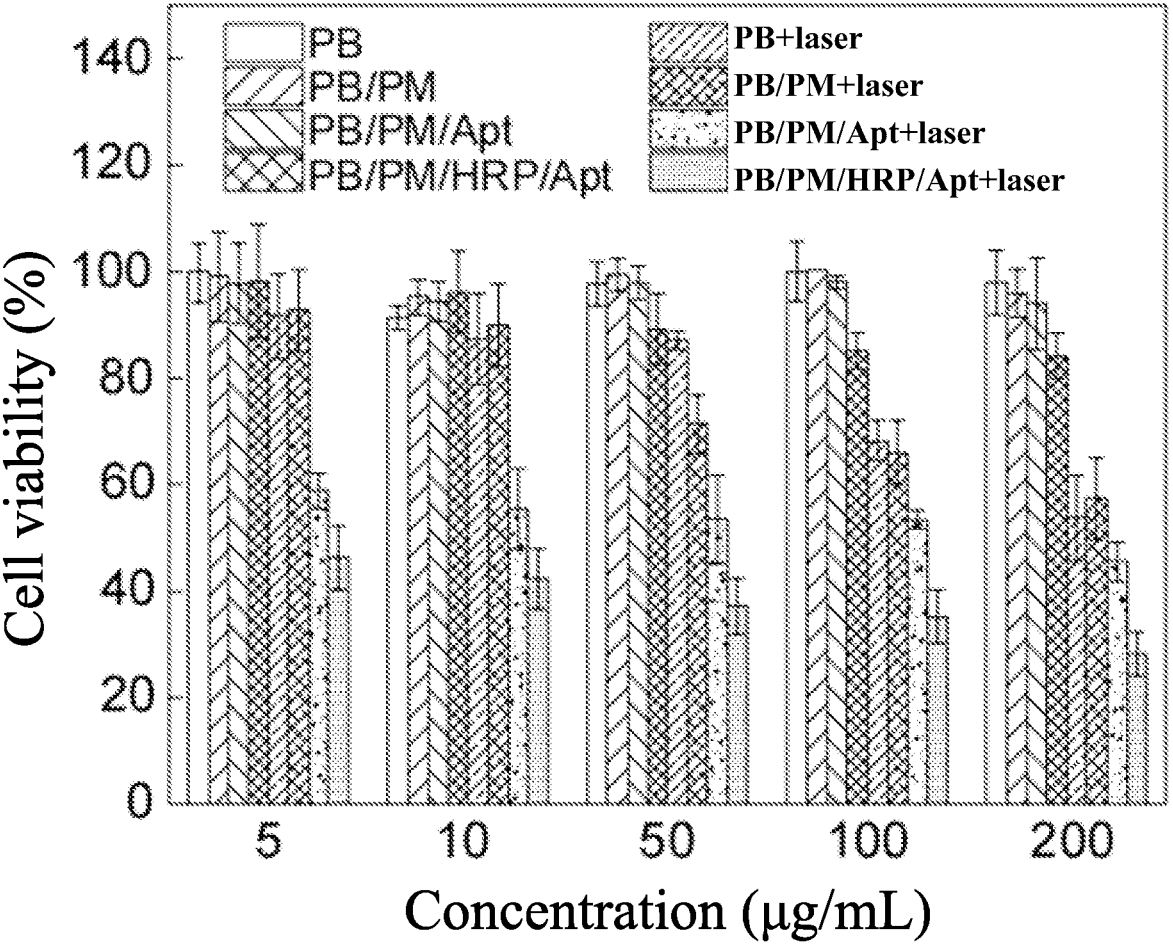
FIG. 10 shows the viability of 4T1 cells treated with different treatment groups.

To further explore the cytotoxicity and biosafety of the nanocomposite, breast cancer cells (4T1) were used for the study by standard cell proliferation/toxicity assay (CCK-8). 4T1 cells were treated with PB of different concentrations (PB: 200 µg/mL, 100 µg/mL, 50 µg/mL, 10 µg/mL, and 5 µg/mL), PB/PM, PB/PM/Apt, and PB/PM/HRP/Apt for 4 h. As shown in FIG. 10, the survival rates of 4T1 cells treated with PB, PB/PM, PB/PM/Apt, and PB/PM/HRP/Apt were all about 90%, and the cytotoxicity was almost negligible, indicating that the prepared PB/PM/HRP/Apt had desirable biocompatibility. After near-infrared (NIR) laser irradiation, the viability of cells treated with PB/PM was significantly weaker compared with that of cells treated with PB, suggesting that the specific targeting of PM to tumor could enhance a therapeutic effect on tumor cells. The survival rate of the PB/PM/Apt+laser group was lower than that of the PB+laser or PB/PM+laser group alone, which might be due to the dual targeting of AS1411 aptamer and PM on cancer cells that increased the accumulation of nanomaterial at the tumor site. In the PB/PM/HRP/Apt group, the survival rate of 4T1 cells was about 28% after 808 nm near-infrared laser treatment. This result indicated that the efficient movement of the nanocomplexes under fuel could effectively enhance a binding efficiency with biological targets, thereby improving the therapeutic efficacy. Obviously, PB/PM/HRP/Apt quickly reached the target cells under the camouflage of PM coating, and exerted a chemical driving effect of HRP, which was combined with PTT therapy to cause devastating damage to cancer cells, thus effectively inhibiting or even killing the cancer cells.

Figure 11:
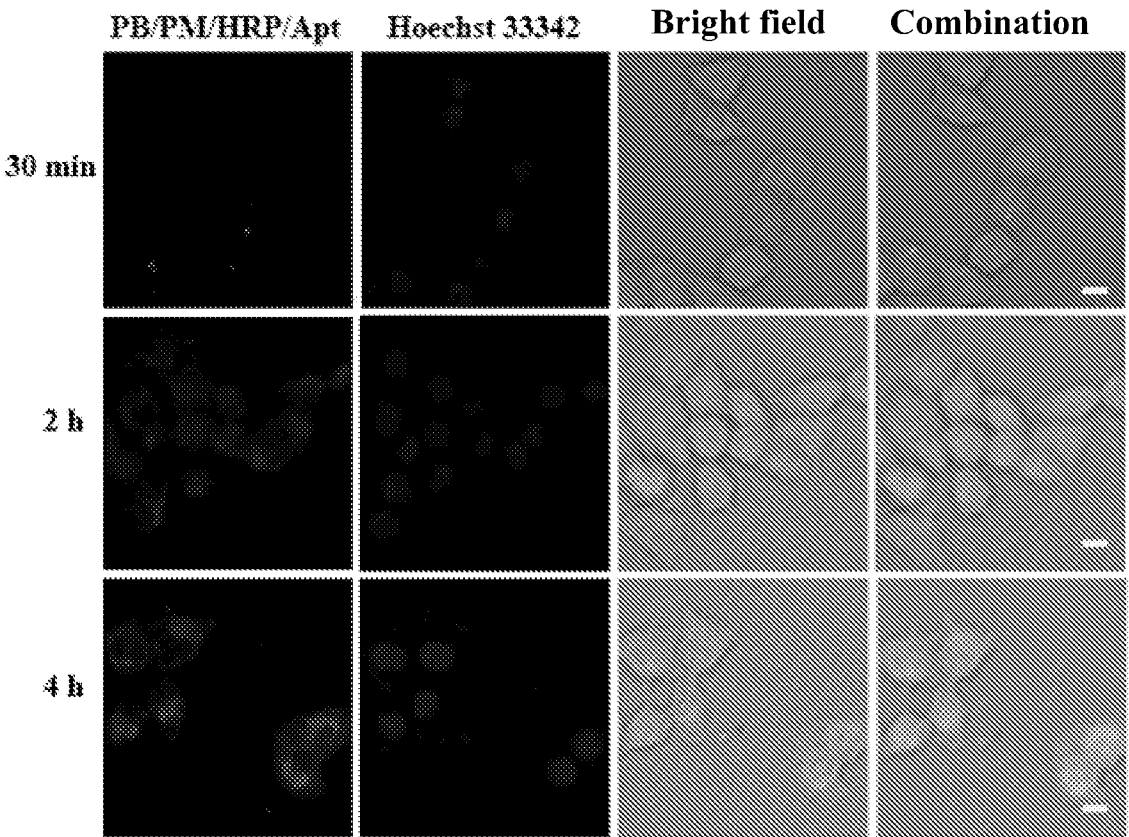
FIG. 11 shows fluorescence imaging of PB/PM/HRP/Apt acting on 4T1 cells after cultured for different time (scale bar: 10 m).

From the above results, it was seen that PB/PM/HRP/Apt combined with laser irradiation had the strongest ability to induce the relevant apoptosis of 4T1 cells. In order to prove that PB/PM/HRP/Apt could effectively target tumor cells and accelerated phagocytosis, 4T1 cells were used to study the cellular internalization of PB/PM/HRP/Apt. PB/PM/HRP/Apt was separately incubated with 4T1 cells for 30 min, 2 h, and 4 h, and a Hoechst 33342 fluorescent dye was added to stain the nuclei for 10 min. Through the bright field, fluorescence images, and superimposed images of confocal laser scanning microscope (CLSM), it was clearly seen that the nucleus of 4T1 cells had blue fluorescence, and the cytoplasm had red fluorescence; and as the incubation time increased, an intensity of the red fluorescence increased (FIG. 11). The results showed that PB/PM/HRP/Apt successfully entered the cytoplasm of 4T1 cells. This demonstrated that PB/PM/HRP/Apt could effectively target tumor cells and successfully enhanced the accumulation of nanocomposite in tumor cells by the propulsion properties.

Although the above embodiments have described the present disclosure in a thorough manner, it is only some but not all embodiments of the present disclosure, and other embodiments may be obtained without inventive step according to the present embodiments, all of which fall within the scope of protection the present disclosure.

plate; subjecting the horseradish peroxidase (HRP) and the PB/PM nanoparticles to a dehydration condensation; and separating a product after the dehydration condensation from the well of the plate to obtain PB/PM/HRP; and 3) mixing the PB/PM/HRP and the aptamer specific for the cancer cells to obtain the nanocomposite.

5. The method according to claim 4, wherein the cancer cells comprise breast cancer cells.

6. The method according to claim 5, wherein the aptamer comprises an AS1411 aptamer.

7. The method according to claim 4, wherein the platelet membrane is prepared from platelets; 80 μL to 120 μL of the platelet membrane is prepared from per $1 \times 10^6$ of the platelets; the Prussian blue nanoparticles are dissolved in a phosphate-buffered saline (PBS), with a concentration of 0.5 mg/mL to 0.6 mg/mL; and the platelet membrane and the Prussian blue nanoparticles have a volume ratio of (1.2-1.5): 1.

8. The method according to claim 5, wherein the platelet membrane is prepared from platelets; 80 μL to 120 μL of the platelet membrane is prepared from per $1 \times 10^6$ of the platelets; the Prussian blue nanoparticles are dissolved in a phosphate-buffered saline (PBS), with a concentration of 0.5 mg/mL to 0.6 mg/mL; and the platelet membrane and the Prussian blue nanoparticles have a volume ratio of (1.2-1.5): 1.

9. The method according to claim 6, wherein the platelet membrane is prepared from platelets; 80 μL to 120 μL of the platelet membrane is prepared from per $1 \times 10^6$ of the platelets; the Prussian blue nanoparticles are dissolved in a phosphate-buffered saline (PBS), with a concentration of 0.5 mg/mL to 0.6 mg/mL; and the platelet membrane and the Prussian blue nanoparticles have a volume ratio of (1.2-1.5): 1.

10. The method according to claim 4, wherein the aptamer is a carboxyl-modified aptamer.

---

---

What is claimed is:

1. A nanocomposite, wherein the nanocomposite material is comprises Prussian blue nanoparticles wrapped by a platelet membrane, and, wherein a surface of the platelet membrane is modified with an aptamer specific for cancer cells and horseradish peroxidase.

2. The nanocomposite according to claim 1, wherein the cancer cells comprise breast cancer cells.

3. The nanocomposite according to claim 2, wherein the aptamer comprises an AS1411 aptamer.

4. A method of preparing the nanocomposite according to claim 1, comprising:

1) Mixing the platelet membrane (PM) and the Prussian blue (PB) nanoparticles to obtain PB/PM nanoparticles;

2) attaching the PB/PM nanoparticles to a well of a plate with a layer of polylysine at the bottom of the well, and adding the horseradish peroxidase to the well of the

11. The method according to claim 5, wherein the aptamer is a carboxyl-modified aptamer.

12. The method according to claim 6, wherein the aptamer is a carboxyl-modified aptamer.

13. The method according to claim 4, wherein the PB/PM/HRP and the aptamer have a mass ratio of (65-70):1.

14. The method according to claim 5, wherein the PB/PM/HRP and the aptamer have a mass ratio of (65-70):1.

15. The method according to claim 6, wherein the PB/PM/HRP and the aptamer have a mass ratio of (65-70):1.

16. The method according to claim 10, wherein the PB/PM/HRP and the aptamer have a mass ratio of (65-70):1.

17. The method according to claim 11, wherein the PB/PM/HRP and the aptamer have a mass ratio of (65-70):1.

18. The method according to claim 12, wherein the PB/PM/HRP and the aptamer have a mass ratio of (65-70):1.

19. The method according to claim 10, wherein the horseradish peroxidase is labeled with biotin; and the PB/PM nanoparticles and the biotin-labeled horseradish peroxidase have a mass ratio of (55-60):1.

20. An antitumor drug, comprising the nanocomposite according to claim 1.

* * * * *